ically associated with the matrix. The antimicrobial
United States Patent

Sawan et al.

[11] Patent Number: 5,817,325
[45] Date of Patent: Oct. 6, 1998

[54] CONTACT-KILLING ANTIMICROBIAL DEVICES

[75] Inventors: Samuel P. Sawan, Tyngsboro, Mass.; Tadmor Shalon, Brentwood, Mo.; Sundar Subramanyam, Stoneham; Alexander Yurkovetskiy, Acton, both of Mass.

[73] Assignees: Biopolymerix, Inc., Farnham, United Kingdom; Surfacine Development Company, L.L.C., Tyngaboro, Mass.

[21] Appl. No.: 742,580

[22] Filed: Oct. 28, 1996

Related U.S. Application Data

[63] Continuation-in-part of Ser. No. 663,269, filed as PCT/US94/14636, Dec. 19, 1994, Pat. No. 5,824,325.

[51] Int. Cl.⁶ .................................................. A01N 25/10
[52] U.S. Cl. .................... 424/411; 424/406; 424/407; 424/422; 424/78.09; 424/78.34; 424/78.35; 424/612; 424/618; 514/495; 514/634; 514/635
[58] Field of Search .................................. 424/404–407, 424/411, 412, 422, 78.09, 78.12, 78.34, 78.35, 443, 446, 447, 617, 618, 619; 514/492–505, 634, 635; 600/29, 36–38, 101, 184; 606/1; 623/1–4, 7, 9–11; 523/122

[56] References Cited

U.S. PATENT DOCUMENTS

| | | | |
|---|---|---|---|
| 3,803,810 | 4/1974 | Rosenberg | 55/159 |
| 4,150,171 | 4/1979 | Feldstein | 427/54 |
| 4,304,894 | 12/1981 | Andrews et al. | 526/310 |

(List continued on next page.)

FOREIGN PATENT DOCUMENTS

| | | | |
|---|---|---|---|
| 1087977 | 10/1980 | Canada | C14C 5/00 |
| 0459498A1 | 12/1991 | European Pat. Off. | A61F 9/00 |
| 2830977A1 | 1/1980 | Germany | A61J 1/100 |
| 61-8104 | 1/1986 | Japan | B01D 13/00 |
| 2-68105 | 3/1990 | Japan | B01D 38/14 |
| 63-218558 | 3/1990 | Japan | B01D 38/14 |
| 2-192937 | 7/1990 | Japan | B23B 15/08 |
| 3065223 | 3/1991 | Japan | B01D 69/00 |
| 4-197362 | 7/1992 | Japan | A61M 25/00 |
| 4-197363 | 7/1992 | Japan | A61M 25/00 |
| 4-709935 | 11/1992 | Japan | G06F 11/32 |
| 5033217 | 2/1993 | Japan . | |
| 8176517 | 7/1996 | Japan . | |
| 2254340 | 7/1992 | United Kingdom | C23C 18/20 |
| 2254340 | 10/1992 | United Kingdom | C23C 18/20 |
| 90/05110 | 5/1990 | WIPO | B67D 5/58 |
| 93/22320 | 11/1993 | WIPO | C07F 9/09 |

OTHER PUBLICATIONS

Boaroni et al., "Case Study: Development of a Device with a Antimicrobial Treatment", Medical Plastics Today and Tomorrow Proc. Med. Plast. Conf., Publ. Soc. Plastics Engineers, Brookfield, CT, 1990.

Chu et al., "Newly Made Antibacterial Braided Nylon Sutures. I. In Vitro Qualitative and In Vivo Preliminary Biocompatibility Study", *J. Biomed. Materials Res.* 21:1281–1300 (1987).

(List continued on next page.)

*Primary Examiner*—Neil S. Levy
*Attorney, Agent, or Firm*—Testa, Hurwitz & Thibeault, LLP

[57] ABSTRACT

Contact killing antimicrobial articles, devices and formulations are described which kill microorganisms on contact. The articles, devices or formulations contain a non-leaching antimicrobial material which is a unique combination of an organic matrix having biocidal metallic materials non-leachably associated with the matrix. The antimicrobial material may used to form an antimicrobial coating or layer on a surface of the article or device, or may be dispersed in a vehicle or carrier to form a topical antiseptic or disinfectant, or solid shape having contact killing antimicrobial properties. When a microorganism contacts the article, device, or formulation, the biocidal metallic material is transferred to the microorganism in amounts sufficient to kill it.

9 Claims, 3 Drawing Sheets

U.S. PATENT DOCUMENTS

| | | | |
|---|---|---|---|
| 4,463,880 | 8/1984 | Kramer et al. | 222/189 |
| 4,494,663 | 1/1985 | Bertaud et al. | 215/232 |
| 4,533,068 | 8/1985 | Meierhoefer | 222/189 |
| 4,563,485 | 1/1986 | Fox, Jr. et al. | 523/113 |
| 4,581,028 | 4/1986 | Fox, Jr. et al. | 623/2 |
| 4,592,920 | 6/1986 | Murtfeldt | 427/2 |
| 4,603,152 | 7/1986 | Laurin et al. | 604/265 |
| 4,612,337 | 9/1986 | Fox, Jr. et al. | 523/113 |
| 4,675,347 | 6/1987 | Mochizuki et al. | 523/122 |
| 4,677,143 | 6/1987 | Laurin et al. | 523/122 |
| 4,769,013 | 9/1988 | Lorenz et al. | 604/265 |
| 4,853,978 | 8/1989 | Stockum | 2/167 |
| 4,882,232 | 11/1989 | Bugnet et al. | 428/613 |
| 4,917,271 | 4/1990 | Kanner et al. | 222/189 |
| 4,938,389 | 7/1990 | Rossi et al. | 222/189 |
| 4,973,493 | 11/1990 | Guire | 427/2 |
| 4,979,959 | 12/1990 | Guire | 623/66 |
| 5,002,582 | 3/1991 | Guire et al. | 623/66 |
| 5,013,459 | 5/1991 | Gettings et al. | 210/764 |
| 5,019,096 | 5/1991 | Fox, Jr. et al. | 623/1 |
| 5,025,957 | 6/1991 | Ranalletta et al. | 222/189 |
| 5,040,706 | 8/1991 | Davids et al. | 222/541 |
| 5,049,139 | 9/1991 | Gilchrist | 604/265 |
| 5,060,823 | 10/1991 | Perlamn | 222/1 |
| 5,069,907 | 12/1991 | Mixon et al. | 424/445 |
| 5,074,440 | 12/1991 | Clements et al. | 222/189 |
| 5,105,993 | 4/1992 | La Haye et al. | 222/189 |
| 5,110,470 | 5/1992 | Yokosawa et al. | 210/500.23 |
| 5,224,493 | 7/1993 | Sawan et al. | 128/832 |
| 5,232,687 | 8/1993 | Geimer | 424/45 |
| 5,265,770 | 11/1993 | Matkovich et al. | 210/189 |
| 5,490,938 | 2/1996 | Sawan et al. | 210/651 |

OTHER PUBLICATIONS

Clark et al., "Antibaterial Vascular Grafts with Improved Thromboresistance", *Arch. Surg.* 109:159–162 (1974).

Nakashima et al Bokin Bobai (1991) 19(9), 451–8.

Amos et al., "Suface Modification of Polymers by Photochemical Immobilization" (Abstract) The 17th Annual Meeting of the Society for Biomaterials, Scottsdale, AZ, May 1–5, 1991.

Bain et al., "Formation of Monolayer Films by the Sponyaneous Assembly of Organic Thiols from Solution onto Gold" *J. Am. Chem. Soc. 11*:321–335 (1989).

Clapper et al., "Covalent Immobilization of Cell Adhesion Proteins and Peptides to Promote Cell Attachment and Growth on Biomaterials" (Abstract), The 16th Meeting of the Society for Biomaterials, Charleston, SC, May 20–23, 1990.

Clapper et al., "Covalent Immobilization of Extracellular Matrix Peptides to Promote Cell Attachment and Growth on Biomaterials" (Abstract), The 16th Meeting of the Society for Biomaterials, Charleston, SC, May 20–23, 1990.

Clapper et al., "Hirudin Immoblization to Produce Antithromobtic Sufaces" (Abstract), Cardiovascular Science and Technology: Basic and Applied, Louisville, KY, Dec. 1–3, 1990.

Colby et al., "Light Activated Polymers for Flexible Surface Modification" (Abstract), Proceedings of the Medical Design and Manufacturing Conference, New York, NY, Jun. 3, 1992.

Davis et al., "Electrode and Bacterial Survival with Iontophoresis in Synthetic Urine" *J. Urology* 147:1310–1313 (1992).

Dunkirk et al., "Photochemical Coatings for the Prevention of Bacterial Colonization" *J. Biomaterials Applications* 6:131–156 (1991).

Dunkirk et al., "Contact Lens Coatings for Increased Wettability and Reduced Deposits and Bacterial Colonization" (Abstract), The 16th Annual Meeting of the Society for Biomaterials, Charleston, SC, May 20–23, 1990.

Erck et al., "Adhesion of Silver Films to Ion–Bombarded Zirconia" *Lubrication Engineering* 47(8):640–644 (1991).

Erdemir et al., "Ion–Assisted Deposition of Silver Films on Ceramics for Friction and Wear Control" *J. Soc. Tribologists and Lubrication Engineers* pp. 23–30 (1990).

Farrah et al., "The Production of Antibacterial Tubing, Sutures and Bandages by in Situ Precipitation of Metallic Salts" *Can. J. Microbiol.* 37:445–449 (1991).

Gravens et al., "The Antibacterial Effect of Treating Sutures with Silver" *Surgery* 73:(1):122–127 (1973).

Herruzo–Cabrera, R., "Evaluation of the Penetration Strength, Bactericidal Efficacy and Spectrum of Action of Several Antimicrobial Creams Isolated Microorganisms in a Burn Centre", *Burns* 18(1):39–44 (1992).

Laibinis et al., "Comparison of the Structures and Wetting Properties of Self–Assembled Monolayers of n–Alkanethiols on the Coinage Metal Sufaces, Cu, Ag, $Au^{1"}$", *J. Am. Chem. Soc.* 113:7152–7167 (1991).

Leung et al., "Decreased Bacterial Adherence to Silver––Coated Stent Material: An in Vitro Study" *Gastrointestinal Endoscopy* 38(3):338–340 (1992).

Liedberg et al., "Silver Coatings of Urinary Catheters Prevents Adherence and Growth of Pseudomonas Aeruginosa" *Urol. Res.* 17:357–358 (1989).

Liedberg et al., "Assessment of Silver–Coated Urinary Catheter Toxicity by Cell Culture" *Urol. Res.* 17:359–360 (1989).

Mastrototaro et al., "Rigid and Flexible Thin–Film Multi––Electrode Arrays for Tansmural Cardiac Recording" *IEEE Transactions on Biomedical Engineering* 39:271–279 (1992).

Pyle et al., "Efficacy of Copper and Silver Ions with Iodine in the Inactivation of Pseudomonas Cepacia" *J. Appl. Bact.* 72:71–79 (1992).

Smoot et al., "Surface Modification of Membranes for Medical and Industrial Applications" (Abstract), The 201st American Chemical Society National Meeting, Atlanta, GA, Apr. 14–19, 1991.

Swanson et al., "Suface Modification of Membranes for Medical and Industrial Applications" (Abstracts), The 201st American Chemical Society National Meeting, Atlanta, GA Apr. 14–19, 1991.

Tsai et al., "In Vitro Quantitative Study of Newly Made Antibacterial Braided Nylon Sutures" *Surgery, Gynecology & Obstetrics* 165:207–211 (1987).

Williams et al., "The Biocompatibility of Silver" *CRC Crit. Rev. Biocompat.* 5(3):221–243 (1989).

Zanoni et al., "A Comparison of Silver Nitrate with Erythromycin for Prophylaxis Against Ophthalmia Neonatorum" *Clinical Pediatrics* pp. 295–298 (1992).

Bio–Metrics Systems, Inc., "Photolink™ Surface Modification for Medical Devices", Technical Bulletin.

Bio–Metrics Systems, Inc., "Photolink™ Modification and Immobilization Technology", Technical Bulletin, 1991.

CONTACT-KILLING ANTIMICROBIAL DEVICES

RELATED APPLICATIONS

This application is a continuation-in-part of U.S. Ser. No. 08/663,269 now U.S. Pat. No. 5,824,325 filed Dec. 13, 1996 which was filed Dec. 19, 1994 as International application no. PCT/US94/14636, which claims priority to U.S. Ser. No. 08/220,821, filed Mar. 31, 1994 (now abandoned) and U.S. Ser. No. 08/170,510, filed Dec. 20, 1993 (now issued as U.S. Pat. No. 5,490,938), the entire disclosures of which are incorporated herein by reference.

FIELD OF THE INVENTION

The present invention relates to devices coated with or containing unique non- leaching antimicrobial materials capable of killing microorganisms on contact, as well as methods of manufacture and use of such materials.

BACKGROUND OF THE INVENTION

The constant threat of bacterial contamination and the associated repercussions on health have made preservatives a ubiquitous part of drugs and packaged food. However, preservatives oftentimes have undesirable side effects, especially in pharmaceutical products. Growing consumer awareness about the deleterious effect of preservatives in recent years has necessitated their reduction or preferably, total elimination, without risking bacterial contamination, thus prompting the need for the development of new, cost effective packaging and storing methods that prevent bacterial contamination. The problem is acute in the pharmaceutical area, especially in the ophthalmic industry, which is presently driven by the need to address the issue of patient sensitivity toward preservatives in ocular solutions. Burnstein, N. L. et al., Trans. Ophthalmol. Soc. 104: H02 (1985); Collins, H. B. et al., Am. J. Optom. & Physiolog. Optics, 51: 215 (A89). Similar problem, exist in the food, medical device, healthcare and water purification areas.

The modality of action of all infection resistant surfaces presently known is via one of the following mechanisms: (i) dissolution of an antimicrobial component into the contacting solution, or (ii) chemically bound antimicrobials. The former is accomplished by blending an antimicrobial compound with a plastic material. The composite material is then either molded into a device or applied as a coating. The bactericidal action of such coatings depend on diffusion of the biotoxic agent into solution. Numerous examples of this type have been reported in the literature. Another variant of this type involves hydrolysis or dissolution of the matrix containing an antimicrobial compound, thereby effecting it's release into solution. High levels of preservatives are, however, released into contacting solutions in long term applications. In the latter mechanism, a bioactive compound is covalently bound either directly to the substrate surface or a polymeric material that forms a nondissolving surface coating. The antimicrobial compounds in such coatings exhibit greatly diminished activity, unless assisted by hydrolytic breakdown of either the bound antimicrobial or the coating itself. In either case, relatively high levels of preservative has to be released into solution in order to elicit antimicrobial action.

Various products for use externally or internally with humans or animals can serve to introduce bacterial, viral, fungal or other undesirable infections. Such products include medical devices, surgical gloves and implements, catheters, implants and other medical implements. To prevent such contamination, such devices can be treated with an antimicrobial agent. Known methods of preparing an infection- resistant medical devices have been proposed in U.S. Pat. Nos. 3,566,874; 3,674,901; 3,695,921; 3,705,938; 3,987,797; 4,024,871; 4,318,947; 4,381,380; 4,539,234; 4,612,337; 3,699,956; 4,054,139; 4,592,920; 4,603,152; 4,667,143 and 5,019,096. However, such methods are complicated and unsatisfactory. Prior known antimicrobial coatings often leach material into the surrounding environment. Many are specifically designed for releasing antimicrobial agents (see, U.S. Pat. No. 5,019,096). There is a need for medical devices and other products which are able to resist microbial infection when used in the area of the body to which they are applied, which provide this resistance over the period of time, and which do not leach antimicrobial materials into the environment.

SUMMARY OF THE INVENTION

It is an object of the invention to provide devices, articles and surfaces coated with and/or containing contact killing non-leaching antimicrobial materials which are capable of killing microorganisms on contact, but which do not leach significant amounts of antimicrobial materials into the surrounding environment. The antimicrobial materials may be deposited on the surface of a substrate to form a contact-killing antimicrobial coating on the surface, may be cast into a freestanding antimicrobial film, or may be incorporated into a carrier to provide a bulk antimicrobial which can be applied as desired to form a contact-killing antimicrobial layer.

The articles, devices and surfaces of the present invention are coated with, or contain (for example, dispersed throughout the article) antimicrobial materials which are molecularly designed to enable a matrix bound biocide to retain high activity without elution of any compounds into contacting solutions, carriers or other materials. The antimicrobial's activity stems from the sustained, cooperative biocidal action of its components. Selective transfer of one component from within the matrix directly to the microorganism upon contact is achieved via a "hand off" mechanism upon engagement and penetration of the microorganism's cell membrane. The antimicrobial material, therefore, maintains long term efficacy without releasing toxic elutables into the surrounding environment.

The antimicrobial material of the present invention comprises a combination of an organic material which forms a matrix, and a broad spectrum biocide intercalated in the matrix that interacts sufficiently strongly with the organic material that the biocide does not leach from the matrix. The organic material must possess two important properties: it must be capable of reversibly binding or complexing with the biocide, and must be capable of insinuating the biocide into the cell membrane of the microorganism. The organic material preferably is capable of dissolving into or adhering to the cell membrane surrounding the microorganism. Preferred organic materials are those which can be immobilized on a surface and which bind the biocide in such a manner as to permit release of the biocide into the microorganism but not into the surrounding environment. The biocide preferably is a low molecular weight metallic material that is toxic to microorganisms and is capable of complexing with or reversibly binding to the organic matrix material, but which binds preferentially to cellular proteins of microorganisms. When a microorganism contacts the antimicrobial material, the organic material engages or penetrates at least the outer portion of the lipid bilayer of the microorganism's cell membrane sufficiently to permit insinuation of the biocide into the microorganism, where cell proteins or proteins in the lipid bilayer compete effectively for the biocide due to favorable binding constants. The result is a contact-killing delivery system that selectively transfers the biocide through or into the microorganism's cell membrane upon contact without elution of the biocide into solution, thereby maintaining long term efficacy. The unique mode of action of the presently described antimicrobial material offers high surface activity coupled with substantially low leachables.

The invention provides for the first time cooperative bioactivity in a contact killing, nonleaching system.

Organic materials useful in the present invention comprise materials which are capable of: 1.) reversibly binding or complexing with a biocide, and 2.) insinuating the biocide into the cell membrane of the microorganism upon contact. A preferred class of materials are those having the aforementioned properties, and which are capable of complexing and/or binding a bactericidal metallic material. Most preferred is the class of organic materials which can dissolve into, or adhere to, and penetrate at least the outer portion of the lipid bilayer membrane of a microorganism. For this purpose, surface active agents, such as cationic compounds, polycationic compounds, anionic compounds, polyanionic compounds, non-ionic compounds, polynonionic compounds or zwitterionic compounds are useful. Organic materials which currently are most preferred for use in the invention include cationic or polycationic materials such as biguanide compounds.

In a preferred embodiment of the present invention, the organic material is crosslinked to form the matrix. Crosslinking agents which can be used in the present invention are those which react with the polycationic material to form a crosslinked network or matrix. Suitable crosslinking agents include, for example, organic multifunctional groups such as isocyanates, epoxides, carboxylic acids, acid chlorides, acid anhydrides, succimidyl ether aldehydes, ketones, alkyl methane sulfones, alkyl trifluoromethane sulfonates, alkyl paratoluene methane sulfones, alkyl halides and organic multifunctional epoxides. In a currently preferred embodiment, the organic material comprises a polyhexamethylene biguanide polymer which is crosslinked with an epoxide, such as N,N-bismethylene diglycidylaniline, to form a crosslinked network or matrix.

The biocidal material can be any antimicrobial material which is capable of non-leachably binding to or complexing with an organic matrix, but which, when placed in contact with the microorganism, preferentially transfers to proteins in the microorganism. For this purpose, metallic materials which bind to cellular proteins of microorganisms and are toxic to the microorganisms are preferred. The metallic material can be a metal, metal oxide, metal salt, metal complex, metal alloy or mixture thereof Metallic materials which are bactericidal or bacteriostatic are preferred. By a metallic material that is bacteriostatic or bactericidal is meant a metallic material that is bacteriostatic to a microorganism, or that is bactericidal to a microorganism, or that is bactericidal to certain microorganisms and bacteriostatic to other microorganisms. Examples of such metals include, e.g., silver, zinc, cadmium, lead, mercury, antimony, gold, aluminum, copper, platinum and palladium, their salts, oxides, complexes, and alloys, and mixtures thereof The appropriate metallic material is chosen based upon the use to which the device is to be put. The preferred metallic materials are silver compounds. In a currently preferred embodiment, a silver halide is used, most preferably, silver iodide.

The invention further comprises liquid compositions for forming a contact killing, non-leaching antimicrobial layer or coating on a surface. In one embodiment, the composition is a two-part composition comprising a first solution, dispersion or suspension of an organic material, and a second solution, dispersion or suspension of a biocidal material. If a crosslinked coating or film is desired, the first solution, dispersion or suspension also will contain the crosslinking agent. As a first step, the crosslinking agent and the organic material may be reacted to form a non-crosslinked adduct. To form a contact-killing nonleaching coating or layer on a substrate, the first composition is applied to the substrate under conditions sufficient to immobilize the organic material on the substrate, forming a matrix. If a crosslinking agent is present, the matrix is cured to induce crosslinking. The matrix then is exposed to the solution of the biocidal material under conditions sufficient induce the biocidal material to become non-leachably attached to, complexed with or associated with the matrix.

In another embodiment, the liquid composition is a one part composition comprising a solution, dispersion or suspension of the organic material, the biocidal material, and optionally, the crosslinker. To form the contact-killing coating on a substrate, this composition is applied to the substrate under conditions sufficient to immobilize the organic material on the substrate, forming a matrix in which the biocidal material is non-leachably attached to or associated with the matrix.

Both the two part composition and the one part composition also may be used to make freestanding antimicrobial films, as described in more detail below. As used herein, the term "freestanding" means not attached to a substrate.

The invention further provides methods for making the compositions of the present invention, and applying them to various substrates to form antimicrobial coatings or layers on the substrates. The method for making the composition generally comprises providing a solution, dispersion or suspension an organic material, and, if a non-crosslinked material is desired, applying the solution, dispersion or suspension of the organic material to the substrate to form the matrix. The organic compound may be attached to and/or immobilized on the substrate by any appropriate method, including covalent bonding, ionic interaction, coulombic interaction, hydrogen bonding, crosslinking (e.g., as crosslinked (cured) networks) or as interpenetrating networks, for example. If a crosslinked coating is desired, the organic material first is combined with a crosslinking agent. Typically, both the organic material and the crosslinker will be in liquid form (e.g., in a solution, dispersion or suspension), and the two solutions are combined, forming a liquid mixture. The liquid may be an organic solvent, an aqueous liquid or a mixture of an organic solvent and an aqueous liquid. The organic material and the crosslinking agent then are reacted to form an adduct. The resulting adduct can be stored for later use, if desired, or can be immediately applied to a substrate. The organic material (with or without the added crosslinker) can be applied to the substrate of choice by any suitable means for applying a liquid coating, including, for example, spraying, brushing, dipping, calendering, rod or curtain coating. The method selected to apply the composition to the substrate will depend on several factors, including the coating thickness desired and the nature and configuration of the substrate. If necessary, the surface to be coated is cleaned or treated before the polymer solution is applied. The resulting coating is dried to form the matrix, or, if a crosslinker is present, subjected to crosslinking conditions, forming a crosslinked network. Crosslinking conditions may include thermal curing, ultraviolet curing, chemical curing or other curing methods. The matrix then is contacted with a solution of the biocidal material under conditions sufficient to deposit the biocidal material into the matrix such that the biocidal material becomes non-leachably associated with or attached to the matrix.

Another embodiment of the method of making the compositions and coatings of the present invention comprises first combining the organic material and the biocidal material, then applying the mixture to the substrate to form the matrix as described above. If a crosslinked coating is desired, the organic material and crosslinking agent are combined and reacted to form an adduct as described above, then the adduct is combined with the biocidal material. The resulting adduct/biocide mixture can be stored for later use, or can be immediately applied to a substrate and cured as described above to induce crosslinking, thereby forming the polymeric network having the biocidal material non-leachably associated therewith or attached thereto.

In the methods of the invention described above, the amounts and/or concentrations of the materials used will depend upon the nature and stoichiometry of the materials used, and the end product desired. In the currently preferred embodiments, the concentration of the solution, dispersion or suspension of the organic material, or the organic adduct resin formed by the reaction of the polymer and crosslinker, typically is in the range of from about 0.5 to about 20% by weight. Typically, a polymer:crosslinker ratio in the range of from about 1:1 to about 3:1 (weight percent) will form crosslinked networks which will non-leachably retain the biocide and preferentially transfer the biocide to the microorganism upon contact as described herein. Solutions of the biocidal material typically comprising from about 0.005 to about 0.5% by weight can be used to impregnate the matrix with biocide.

In another embodiment of the present method, a free-standing antimicrobial film may be formed using the present antimicrobial material. In this embodiment, using the two-part compositions described above, a solution, suspension or dispersion of the organic material is cast on a non-adherent substrate and dried to form a film. If a crosslinked material is desired, the organic material and crosslinker first are combined and reacted to form an adduct as described above, and a solution, suspension or dispersion of the adduct is cast to form the film. The film is cured to induce crosslinking, as described above. The film then is contacted with a solution, dispersion or suspension of the biocidal material to deposit the biocidal material within the matrix of organic material. The film then is detached from the substrate and used as desired. Alternatively, freestanding crosslinked or non-crosslinked films can be cast using the one part liquid compositions described above. In this embodiment, the organic material must have film forming capability so that a coherent film can be obtained free of any substrate. Free-standing antimicrobial materials also may be prepared using the antimicrobial materials of the present invention in other physical forms besides films, such as microbeads or solid shapes, for example.

In another embodiment, an antimicrobial powder may be formed by casting a freestanding film, as described above, then grinding the film to a powder. The powder has the same contact-killing antimicrobial properties as the films and coatings described above. The antimicrobial powder can be incorporated into a carrier, such as a gel, cream or liquid, and applied to a surface to form an antimicrobial layer. For example, a formulation comprising the antimicrobial powder dispersed in a pharmaceutically acceptable carrier can be used as a topical antiseptic and be applied to a wound. The powder also can be dissolved or dispersed in a carrier or vehicle which can be spread, sprayed, wiped or applied in some other manner to form a contact killing antimicrobial layer on a surface or to kill microbes on the surface. The powder also may be compounded into a polymeric material and cast or molded into a solid or semisolid article. The resulting solid or semisolid article has contact killing antimicrobial capability.

In a preferred embodiment, the antimicrobial materials of the present invention is used to form a contact-killing surface on a substrate. To provide the contact-killing surface on the substrate, the organic compound may be attached to and/or immobilized on the substrate by any appropriate method, including covalent bonding, ionic interaction, coulombic interaction, hydrogen bonding, crosslinking (e.g., as crosslinked (cured) networks) or as interpenetrating networks, for example. In a currently preferred embodiment, the organic matrix is formed by first reacting polyhexamethylenebiguanide with N,N-bismethylene diglycidylaniline to form an adduct. Stable coating solutions of the resulting adduct have been obtained in both absolute ethanol and in aqueous ethanol. The adduct can be applied on a substrate surface either by dip-coating, brushing or spraying. Once applied to the substrate, the coating is thermally cured to induce crosslinking, thereby forming a polymeric network on the substrate. The resulting coating is optically clear, resistant to most solvents and to temperature changes, and does not delaminate, flake or crack. The coating typically is about ten microns or less in thickness, although the thickness of the coating may be varied by well- known techniques, such as increasing the solids content of the resin. A broad spectrum metallic antimicrobial, preferably a silver compound, then is introduced into the polymeric network such that it is entrapped as submicron particles, and complexes with the functional groups on the polymer. In the currently preferred embodiment, the broad spectrum antimicrobial is a silver halide, preferably silver iodide.

The antimicrobial materials of the present invention are unique in the following respects:

i) The unique nature of the antimicrobial coating material utilizes a cooperative effect of it's components. This results in high biocidal activity, while maintaining almost no significant leachables into solutions it is in contact with.

ii) The mechanism of action is essentially a surface mediated one, whereby organisms succumb only upon contact with the material due to the non-leaching property associated with it.

iii) The ability of such surfaces to remain completely inert in solution in the absence of microorganism contamination.

iv) The ability of such surfaces to remain viable over multiple organism challenges with no decrease in their bioactivity.

v) The utilization of such biocidal materials on an interior or exterior surface of a device, thereby eliminating the possibility of microbial colonization on the surface.

vi) User friendliness and cost effectiveness of the coating for all types of applications.

vii) Adaptability to existing manufacturing technology, thereby enabling large scale manufacture with minimal cost.

viii) Applicability to a variety of liquid formulations over a wide range of solution viscosity including artificial tears, saline, anti-glaucoma and ocular hypertensension drugs, and contact lens cleaning solutions.

ix) Readily adaptable for the delivery of other types of medicaments or solutions where preservatives have been used such as ear and nasal drug formulations.

The above and other objects, features and advantages of the present invention will be better understood from the following specification when read in conjunction with the accompanying drawings.

BRIEF DESCRIPTION OF THE DRAWINGS

FIG. 2A shows the matrix immobilized on the substrate, with chains of the organic material forming arms or tentacles that protrude into the surrounding environment;

FIG. 2B shows the immobilized matrix impregnated with a biocidal compound, with reservoirs of the biocide deposited within the matrix and molecules of the biocidal compound attached to the tentacles;

FIG. 2C shows a microorganism in contact with the matrixibiocide complex wherein the polymer chains engage and dissolve into the microorganism cell membrane;

FIG. 2D shows penetration of the cell membrane and transfer of the biocide from the network into the microorganism, causing cell death.

DETAILED DESCRIPTION

Figure 1A:
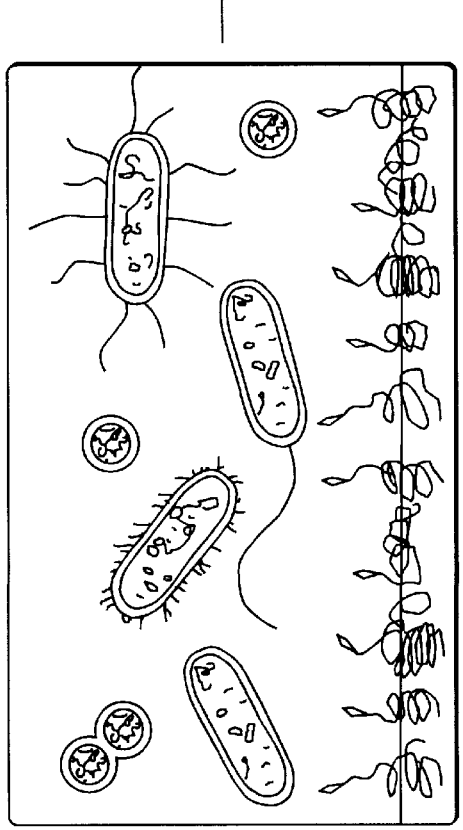
FIG. 1A is a schematic graphic illustration of the matrix/biocide complex of the present invention, before contact of the coating with microorganisms.
Figure 1B:
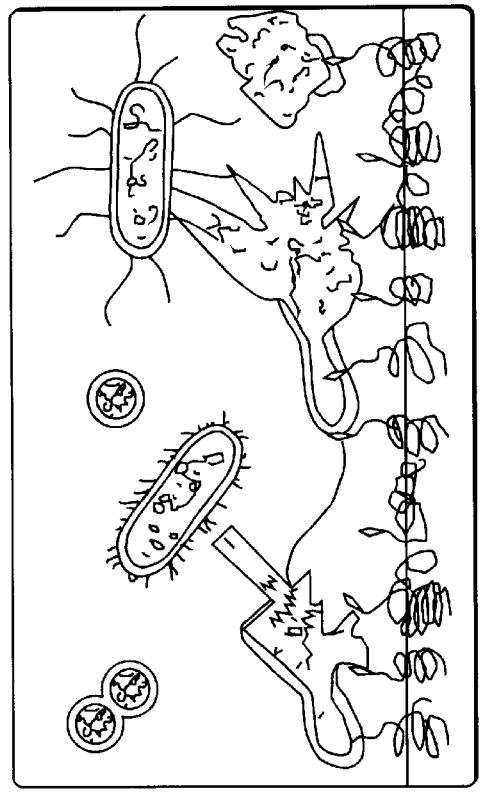
FIG. 1B is a schematic graphic illustration of the contact-killing ability of the matrix/biocide complex of the present invention during contact of the coating with microorganisms.
Figure 2A:
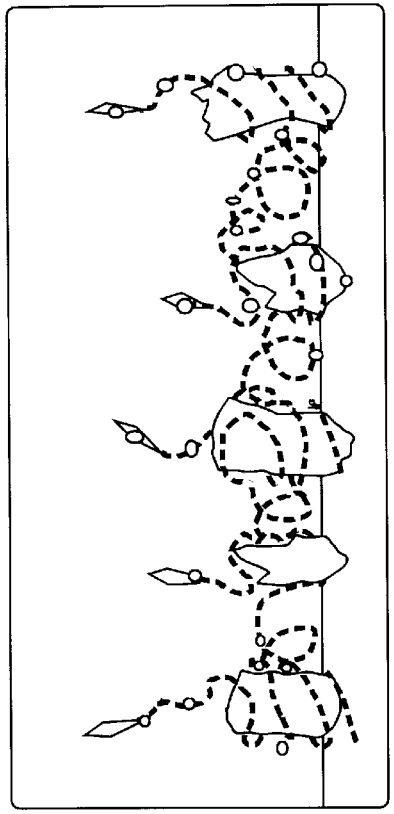
FIGS. 2A–D are a schematic graphic illustration of a preferred method for applying the matrix/biocide complex of the present invention to a substrate.
Figure 2B:
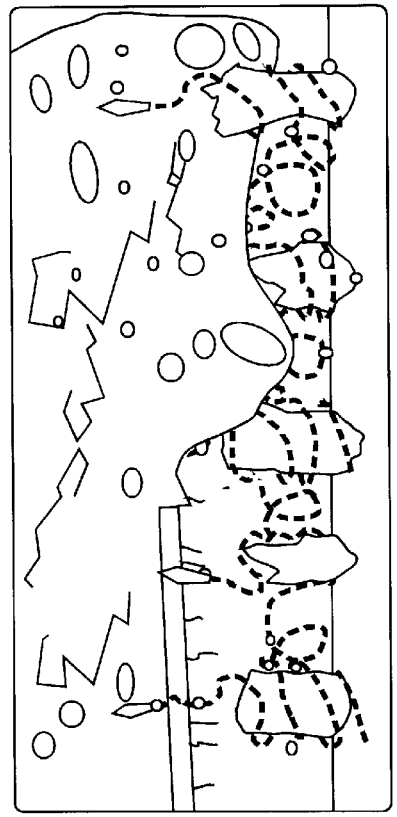
Figure 2C:
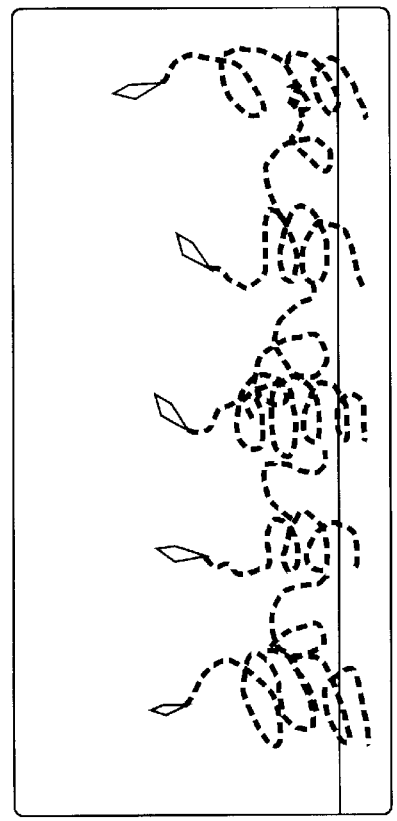
Figure 2D:
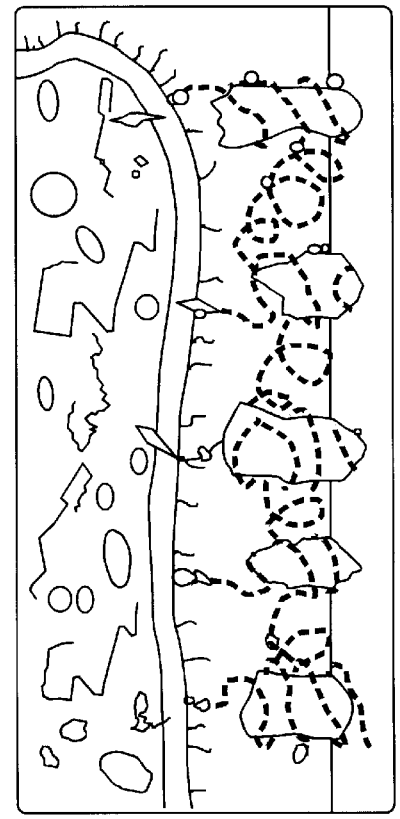

The contact-killing non-leachable antimicrobial materials of the present invention can be applied to a variety of substrates. Antimicrobial coatings according to the present invention can be applied, for example, to woods, metals, paper, synthetic polymers (plastics), natural and synthetic fibers, natural and synthetic rubbers, cloth, glasses, and ceramics. Examples of synthetic polymers include elastically deformable polymers which may be thermosetting or thermoplastic such as, for example, polypropylene, polyethylene, polyvinylchloride, polyethylene terephthalate, polyurethane, polyesters, rubbers such as polyisoprene or polybutadiene, polytetrafluoroethylene, polysulfone and polyethersulfone polymers or copolymers. The substrate can be a deformable metallic or plastic medicament container, such as a toothpaste tube, where the container may remain deformed after each dose is dispensed. Other polymeric materials, including polymeric materials which are used for the preparation of membranes or filter papers, also can serve as substrates. Examples of organic polymeric materials include polyamide (e.g., nylon), polycarbonate, polyacrylate, polyvinylidene fluoride, cellulosics (e.g., cellulose), and Teflon®. The substrate can be either hydrophilic or hydrophobic. With the exception of silicone and Teflon®, which may require prior surface activation with techniques such as plasma, chemical oxidation or metallic sensitization, e.g., a primer, no surface activation is necessary. Inorganic materials to which the present coatings can be applied include glass fiber materials, ceramics such as alumina or silica, and metals. Sintered glass and sintered ceramic substrates also can be used.

The term "microorganism" as used herein includes bacteria, blue-green algae, fungi, yeast, mycoplasmids, protozoa and algae.

The term "biocidal" as used herein means bactericidal or bacteriostatic. The term "bactericidal" as used herein means the killing of microorganisms. The term "bacteriostatic" as used herein means inhibiting the growth of microorganisms, which can be reversible under certain conditions.

As used herein, the terms "non-leachable" or "substantially non-leachable" means that none or very minute amounts (e.g., below a certain threshold) of the organic and/or biocidal material dissolves into a liquid environment. Preferably, this threshold is no higher than I part per million (ppm), and more preferably is lower than 100 parts per billion (ppb).

Organic materials useful in the present invention comprise materials which are capable of: 1.) reversibly binding or complexing with the bactericide, and 2.) insinuating the bactericide into the cell membrane of the microorganism. A preferred class of materials are those having the aforementioned properties, which are capable of being immobilized on a surface and which preferentially bind a bactericidal metallic material in such a manner so as to permit release of the metallic biocide to the microorganism but not to the contacting environment. Most preferred is the class of organic materials which can dissolve into, adhere to, disrupt or penetrate the lipid bilayer membrane of a microorganism. For this purpose, surface active agents, such as cationic compounds, polycationic compounds, anionic compounds, polyanionic compounds, non-ionic compounds, polyanionic compounds or zwitterionic compounds may be used. Organic materials which currently are most preferred for use in the invention include cationic or polycationic compounds such as biguanide compounds. These may be attached to and immobilized on a substrate, or used to form the matrix of a freestanding film, by any appropriate method, including covalent bonding, ionic interaction, coulombic interaction, hydrogen bonding, crosslinking (e.g., as crosslinked (cured) networks) or as interpenetrating networks, for example.

Preferred cationic materials include benzalkoniumchloride derivatives, a-4-[1-tris(2-hydroxyethyl) ammonium-2-butenyl] poly[I-dimethylammonium-2-butenyl]-ω-tris(2-hydroxyethyl) ammonium chloride, and biguanides of the general formula:

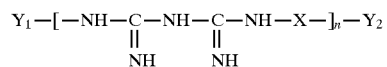

or their water soluble salts, where X is any aliphatic, cycloaliphatic, aromatic, substituted aliphatic, substituted aromatic, heteroaliphatic, heterocyclic, or heteroaromatic compound, or a mixture of any of these, and $Y_1$ and $Y_2$ are any aliphatic, cycloaliphatic, aromatic, substituted aliphatic, substituted aromatic, heteroaliphatic, heterocyclic, or heteroaromatic compound, or a mixture of any of these, and where n is an integer equal to or greater than 1. Preferred compounds include, e.g., chlorhexidine (available from Aldrich Chemical Co., Milwaukee, Wis.) or polyhexamethylene biguanide (available from Zeneca Biocides, Inc. of Wilmington, Del.). The above-mentioned organic materials may be modified to include a thiol group in their structure so as to allow for the bonding of the compound to a metallic substrate, or may be derivatized with other functional groups to permit direct immobilization on a non-metallic substrate. For example, the above-mentioned organic materials may be suitably functionalized to incorporate groups such as hydroxy, amine, halogen, epoxy, alkyl or alkoxy silyl functionalities to enable direct immobilization to a surface.

In a preferred embodiment of the present invention, the organic material comprises a polycationic material which is crosslinked to form the matrix. Crosslinking agents which can be used in the present invention are those which react with the polycationic material to form a crosslinked network or matrix. Suitable crosslinking agents include, for example, organic multifunctional groups such as isocyanates, epoxides, carboxylic acids, acid chlorides, acid anhydrides, succimidyl ether aldehydes, ketones, alkyl methane sulfones, alkyl trifluoromethane sulfonates, alkyl paratoluene methane sulfones, alkyl halides and organic multifunctional epoxides. In a currently preferred embodiment, a polyhexamethylene biguanide polymer is crosslinked with an epoxide, such as N,N-bismethylene diglycidylaniline, to form a crosslinked network.

The biocidal material can be any antimicrobial material which is capable of non-leachably binding to or complexing with the organic matrix, but which, when placed in contact with the microorganism, preferentially transfers to the microorganism. For this purpose, metallic materials which are toxic to microorganisms are preferred. The metallic material can be a metal, metal oxide, metal salt, metal complex, metal alloy or mixture thereof Metallic materials which are bactericidal or bacteriostatic are preferred. By a metallic material that is bacteriostatic or bactericidal is meant a metallic material that is bacteriostatic to a microorganism, or that is bactericidal to a microorganism, or that is bactericidal to certain microorganisms and bacteriostatic to other microorganisms. Examples of such metals include, e.g., silver, zinc, cadmium, lead, mercury, antimony, gold, aluminum, copper, platinum and palladium, their oxides, salts, complexes and alloys, and mixtures of these. The appropriate metallic material is chosen based upon the use to which the device is to be put. The currently preferred metallic materials are silver compounds.

The biocidal material can be introduced into the matrix either contemporaneously with or after application of the organic material to a surface.

The invention also provides for a substrate in which the surface is at least partially coated with additional organic materials, and/or biocidal materials, or both. Examples of organic and biocidal materials that can be used are discussed above. The use of a combination of at least two different organic and biocidal materials can enhance the antimicrobial properties of the coating. Different types of microorganisms can exhibit different degrees of sensitivity to different organic and biocidal materials. In addition, the use of two or more different organic and biocidal materials can significantly reduce the problem of selection for microorganisms having resistance to the organic and biocidal materials in the coating that can occur when only one is used.

The amount and/or type of the antimicrobial coating which is used in a particular application will vary depending on several factors, including the type and amount of contamination which is likely to occur, and the size of the antimicrobial surface. The amount of antimicrobial used will be a minimum amount necessary to maintain the sterility of the liquid. As stated above, this amount will vary depending upon various considerations.

In a preferred embodiment, the organic material, whether crosslinked or non-crosslinked, forms an insoluble, non-leachable matrix having a unique configuration: some of the organic material protrudes into the surrounding environment, that is, "arms" or "tentacles" of the organic material project away from the matrix and into the surrounding environment. This phenomenon can be understood by referring to FIGS. 1 and 2, which are schematic graphic illustrations of a preferred coating of the present invention in which the organic material is a crosslinked biguanide polymer and the biocidal material is a silver halide salt, preferably silver iodide. FIGS. 1A and 1B and FIGS. 2A–D show the polymer matrix having tentacles projecting into the ambient environment, and the silver salt deposited in reservoirs and on the tentacles. Without wishing to be bound by theory, it is believed that when a microorganism contacts the coating, the biguanide polymer tentacles dissolve into the lipid bilayer surrounding the microorganism, thereby introducing silver molecules into the interior of the microorganism or to proteins within the cell membrane. The silver salt has a greater affinity for certain proteins in the microorganism than for the polymer, and therefore complexes with the cellular proteins and is transferred into the microorganism, thereby killing it. Specifically, it is thought that the silver forms complexes with the sulfhydryl and amino groups of the cellular proteins.

In this embodiment, the silver salt is attached to or impregnated into the matrix and on the tentacles of the polymer such that the silver is substantially non-leachable. Again, not wishing to be bound by theory, it is believed that the silver salt forms complexes with functional groups in the polymer, and that the complexed silver resists leaching into ambient liquids or other materials (e.g., creams or gels) in contact with the coated surface. However, when the coating becomes exposed to cellular proteins, the silver preferentially complexes with the proteins.

In a currently preferred embodiment, the polymeric material is polyhexamethylene biguanide, (PHMB), the crosslinking agent is N,N-bismethylenediglycidylaniline (BMDGA), and the silver salt is a silver halide, most preferably, silver iodide. In this embodiment, the coating is made by combining a solution of polyhexamethylene biguanide with a solution of the crosslinking agent, and reacting the mixture under conditions sufficient to form a non-crosslinked PHMB-BMDGA adduct. The ratio of PHMB to BMDGA preferably is in the range of from about 1:1 to 3:1 by weight. The PHMB-BMDGA mixture is heated to about 95° C. for about 2 hours in a closed reactor to form the adduct. The concentration of the resulting adduct resin preferably is in the range of from about 0.5 to about 20% by weight. The adduct resin solution is coated onto the desired substrate, and heated to a temperature sufficient to induce crosslinking between the adducts, thereby forming a crosslinked network or matrix. Temperatures sufficient for crosslinking typically are in the range of from about 70° C. to about 200° C. The resulting crosslinked network is then saturated with silver by immersing the coating for about two minutes in a silver iodide/potassium iodide solution. Silver solutions having a concentration of from about 0.005 to about 0.5% can be used for this step. The silver iodide forms reservoirs in the matrix, and becomes attached to the tentacles. Silver iodide has sufficient affinity for the PHMB polymer that it forms an insoluble complex that will not leach into ambient solutions or other materials in contact with the material, even at elevated temperatures. However, when a microorganism contacts the coating, the tentacles disrupt the microorganism's lipid bilayer membrane, thereby introducing the silver iodide into the microorganism. Silver iodide has greater affinity for certain proteins within the microorganism than for the PHMB-BMDGA matrix, and forms complexes with these proteins, that is, the silver is preferentially transferred from the coating to the microorganism. The silver accumulates to toxic levels in the microorganism and kills it. The silver iodide reservoirs within the matrix replenish the silver iodide on the tentacles lost to the microorganism by reestablishing the equilibrium for formation of the complex (AgI+PHMB$\leftrightarrows$[PHMBAgI]).

This invention also includes the coated substrates, free-standing films, microbeads or other shapes, powders and articles made in accordance with the above methods.

The present invention provides stable, adherent coatings or layers using the present coating formulations on a wide range of materials, including those commonly used in membranes and in medical device manufacture. The coating or layer may be applied directly to most surfaces without prior surface modification. Studies simulating a year of contact between the coating and aqueous solutions at ambient temperature resulted in less than 100 ppb of any active ingredient in the solution. The extract solutions themselves (solutions which have been in contact with the coating) show no antimicrobial or mammalian cell toxicity. The coated surface remains fully inert and bio-active after exposure to various physical and chemical stresses including: low temperature, ethanol, boiling water, prolonged exposure to varying pH solutions and solutions of high ionic strength, as well as sterilization by conventional methods (e.g., wet autoclave, ethylene oxide, $\gamma$-irradiation, ethanol).

Surface coatings, freestanding films, beads and articles and formulations containing the antimicrobial powder or microbeads according to the present invention exhibit antimicrobial activity against both gram positive and gram negative bacteria and yeast, and are resistant to fungal growth. Treated surfaces completely kill organisms at challenge levels of $10^6$–$10^8$ CFU/mL within 8 to 20 hours at 30° C., depending on organism type. Tables 1 and 2 (in Example 4) list the bioactivity of coated surfaces towards different challenge organisms. The coating renders surfaces biofilm resistant, which coupled with its chemical inertness, makes it particularly suited for many device applications.

The antimicrobial materials of the present invention also have been successfully applied on the surface of microporous membranes, including within the pores as evidenced by SEM-EDX. Stable, uniform coatings have been obtained on a variety of membrane materials with almost no reduction in their flow property. Coated microporous membranes kill micro organisms upon contact and are resistant to the phenomenon of "bacterial grow-through" which occurs even in sterilizing 0.2 $\mu$M pore size membranes in long term contact applications. Such membranes are, therefore, well suited for incorporation in devices used in long term filtration applications such as multi-dose dispensers for preservative free formulations, water purification systems and in any application where it is desirable to use barrier properties of a membrane for more than a day.

The mechanism of action is one wherein the antimicrobial materials are activated only upon contact with the microorganism. Once the microorganism accumulates a toxic amount of silver, it succumbs and detaches from the surface. The coating or other treated surface, therefore, remains active only as long as viable organisms contact it, and reverts to being inert in their absence. This unique property whereby the biological activity is triggered by bacterial cell contact enables the coating to function "intelligently." For such a contact mechanism to be valid, the rate of kill is expected to vary as a function of the ratio of total surface area of coated substrate to the volume of the bacterial suspension in contact with it (S/V ratio) at constant temperature. As shown in the Examples, time to kill experiments were performed on coated polyethylene tubes of varying inner diameter that were inoculated with predetermined volumes of a suspension containing $10^6$ CFU/mL of *Pseudomonas aeruginosa* in phosphate buffered saline (PBS). The decrease in organism concentration was measured as a function of time at constant temperature over 20 hours. Experimental results are summarized in FIG. 3. There is no substantial difference in kill rate for S/V ratios ranging from 2.5 to 5 cm$^{-1}$; similar results were obtained for a ratio of 1.5. For the largest diameter tubes tested (S/V =0.5), however, viable organisms were detected at low levels, which can be attributed to a decrease in probability of organisms contacting the surface with increasing volumes. No toxic components were found in organism-free solutions in contact with coated tubes under identical conditions when tested both chemically and biologically, which supports the proposed contact mechanism for cell death. Such a distinction would not be evident if sterilization were to occur via either controlled dissolution or diffusive elution of the coating components into solution; in either case, high levels of active components would be present in solution.

The antimicrobial materials of the present invention can be used to form contact-killing coatings or layers on a variety of substrates. As shown in the Examples, the material forms a non-leaching contact-killing surface on medical devices such as catheters, urological devices, blood collection and transfer devices, tracheotomy devices, intraocular lenses, and on personal care products such as toothbrushes, contact lens cases and dental equipment. The materials can be used on medical devices and healthcare products, baby care products, personal hygiene products, household products, food preparation surfaces and packaging, water storage, treatment and delivery systems, biosensitive systems and laboratory and scientific equipment.

In addition to forming coatings or layers on substrates, the present antimicrobial materials can be used to makes antimicrobial powders, microbeads, or solid shapes. The present antimicrobial materials in powder form or in the form of microbeads, for example, can be dispersed or dissolved in a carrier and used as a topical antiseptic, wound dressing or topical disinfectant. The present antimicrobial materials (e.g., in powder or microbead form) also can be dispersed in a polymeric matrix and used to make plastic articles having contact-killing antimicrobial properties, for example, countertops, shelving material, toilet seats and other bath fixtures, cutting boards and other kitchen materials, and many others.

Contact lens cases are a proven contributor to the spread of ocular pathogens and disease. A lens case coated with a coating of the present invention has been shown in vitro to kill all clinically relevant pathological strains of microorganism without leaching toxic chemicals into the contact lens solution (see Examples 2 and 4) Once a bio-film has formed on an untreated contact lens case, it is resists virtually all types of disinfection products currently available for contact lens care. Thus, the bio-film serves as a reservoir for bacteria that re-contaminate the lens each time it is stored in the case. The treated lens case is compatible with all disinfecting solutions tested to date. Use of the coating permits sterilization of the lenses using ordinary saline as the soaking solution.

The present antimicrobial materials can be used to coat ordinary nylon bristle toothbrushes (see Example 2). The treated toothbrush kills the pathogens commonly found in the human mouth and on bathroom surfaces, while untreated toothbrushes foster their growth. It is believed that toothbrushes are partly responsible for the spread of oral and dental disease. In vitro and in vivo test programs examined the types, number and kill-rates for the organisms commonly found in the mouth. The tests indicated that the treated toothbrush eliminated virtually all of these pathogens over a 12 hour period. The inert coating does not elute from the brush and therefore has no taste and poses no risk to the consumer. The present materials also can be used to provide an antimicrobial layer or to kill microbes on dental instruments, dental floss, and other devices for use in the mouth.

Bio-film formation is a major problem in many water container, water filtration, and water delivery applications. Once a bio-film is formed, it typically resists further treatment and acts as a constant source of microbial contamination. Prevention of bio-film formation is key to the maintenance of high quality water systems. The present materials can be used to prevent bio-film formation on many water treatment products. For example, water containers and water purification systems used in camping, residential, commercial and military applications, which need to be periodically emptied, disinfected and rinsed. Treatment with the present antimicrobial materials would eliminate the costs and hazards associated with this process, as well as the risks associated with improper maintenance of these water storage systems.

The present antimicrobial materials also are useful in point-of-use water purification filters, which trap bacteria and nutrients commonly found in all water systems. The bio-films formed in these filters often shed bacteria into the water stream in quantities exceeding the standard safety limits. Treated filters would offer longer service life and significantly reduce the potential for bio-hazard.

Surfaces in medical offices, such as treatment tables, or consoles in a typical dental office have proven to be a major source of bacterial contamination—posing potential health risks to the patient and staff. Although water supplies are routinely treated to reduce bio-contamination, water standing in the lines in the dental console can promote the formation of bio-films. Coating or treating these surfaces with the antimicrobial materials of the present invention can prevent bio-film formation on these substrates.

The present antimicrobial materials have been tested against the bacteria most commonly found in water. Treated tubing withstood repeated attempts to bio-film formation at very high challenge levels, while untreated control tubing developed extensive bio-film (see Example 5). The treated tubing showed no traces of chemical elution into the water.

The present materials also can be applied to woven and non-woven fabrics used in hospitals and on healthcare supplies ranging from face masks to bed sheets. The materials can be applied in a spray or wipe form which can be applied to surfaces in order to make them antimicrobial.

Long term indwelling catheters pose a risk of infections (2%–9%) which increases patient discomfort, the risk of systemic infections and the length of the patient's hospital stay. Catheters treated with the present antimicrobial materials can reduce the presence of infection causing bacteria. The materials also can be used on urinary catheters, implants and inserts designed to deal with incontinence suffer from increased risk of infection. Coatings made with the present materials have been demonstrated to kill microorganism in human urine.

The antimicrobial materials of the present invention can be used to treat standard biological plastic laboratoryware for applications which require low microbiological contamination, e.g. cell culture lab ware.

EXAMPLES

Example 1

Preparation of PHMB-BMDGA Solutions

Polyhexamethylene biguanide (PHMB) (available as a 20% aqueous solution from Zeneca Biocides, Wilmington, Del.) was distilled to remove the water, and the PHMB was re-dissolved in absolute ethanol to give a 20% by weight solution. This solution was used to prepare the resins outlined below.

(a) 312 mL of the 20% PHMB solution in ethanol was further diluted with 600 ml of ethanol. This solution was added to a solution of N,N-bismethylene diglycidylaniline) (BMDGA) (Aldrich Chemical Company, Milwaukee, Wis.) containing 37.60 grams of BMDGA dissolved in 119.9 ml of acetonitrile and 280.1 ml of ethanol. The resulting mixture was heated at 95° C. in a closed reactor for two hours, forming a PHMB-BMDGA adduct. The adduct solution was cooled and filtered (Scientific Grade 417 filter). The resulting adduct solution contained 10% by weight of PHMB:BMDGA adduct having a PHMB:BMDGA ratio of 1.5:1.

(b) 330 mL of the 20% PHMB. This solution was combined with 100 ml of a sodium hydroxide (NaOH) solution containing 66 grams of NaOH, 66 ml of water and 34 ml of ethanol. This mixture was added to a solution containing 40 grams of BMGDA, 120 ml of acetonitrile and 280 ml of ethanol. The resulting solution was heated at 95° C. for 2 hours forming the PHMB-BMDGA adduct. The solution was cooled and filtered as described above. The resulting adduct solution contained 10% by weight of PHMB:BMDGA adduct having a PHMB:BMDGA ratio of 1.5:1.

The resins were characterized according to the following procedures:

1. Film formation was tested by a dip test with PE/PP (polyethylene/polypropylene) in which PE/PP samples were dipped in the resin solutions made in (a) and (b) above and dried by hot air blowing, and film formation was observed;
2. The ratio of polymer to crosslinker (PHMB-BMDGA) in the resin solution was tested by UV/visible spectroscopy;
3. Gelation time of the resin mixture was tested.

The resins were diluted with ethanol to a concentration of 1%. Film formation of the diluted resins were tested by the dip test with PE/PP as described above. Both resins formed a coherent film. The resins were stored in closed containers at ambient temperature.

Example 2

Coating of Plastic Articles

Various plastic articles were coated using the coating solutions described in Example 1.

1. contact lens cases: polyethylene and polypropylene contact lens cases were coated according to the following procedure:

The contact lens cases were cleaned by immersing them in absolute ethanol for 5 minutes and dried. The cleaned cases were immersed in the antimicrobial coating solution (Example 1a or 1b) for 1 to 2 minutes. The sample cases were dried by hot air blowing. Crosslinking was induced by heating the cases at 120° C. for the polyethylene cases and at 200° C. for the polypropylene cases for 2 hours. The cases were allowed to cool, rinsed with 60° C. water to remove any unbound polymer, then dried at 60° C. for 1–3 hours.

The coated cases were immersed in a 0.05% solution of silver iodide/potassium iodide in alcohol for 2 minutes. The cases were rinsed with aqueous alcohol to remove any unbound silver. The cases then were rinsed with water and dried.

2. Toothbrush bristles: toothbrushes with nylon bristles were coated according to the procedure described for contact lens cases, except that the cross-linking reaction was carried out at 120°–140° C.

3. Polyurethane and Polyvinylchloride Catheters: polyurethane and polyvinyl chloride catheters were coated according to the procedure described for contact lens cases, except that the crosslinking reaction was carried out at 80°–120° C. for polyurethane and at 120° C. for polyvinylchloride.

4. Dental Water Line Unit Tubing And Filters: polyurethane tubing and polyethersulfone membrane and housing were coated according to the procedure described for contact lens cases, except that the crosslinking reaction was carried out at 80°–120° C. for polyurethane and 120°–140° C. for polyethersulfone.

5. Coating Process for Silicone Parts: The parts were pre-cleaned in 100% ethyl alcohol (reagent grade) to remove dirt, grease and other contaminants. They are then subjected to an alkaline etch by immersing them in a 0.1M NaOH in 90% ethanol solution (10% water) at room temperature and ultrasonicated for 2 minutes. They were then coated in an identical manner as the contact lens cases.

6. Coating Process for Teflon Parts: The parts were subjected to surface pretreatment by oxygen plasma for 5 minutes in a plasma reactor. They were then coated in an identical manner as the contact lens cases.

7. Coating Process for Nylon Sheets: Nylon sheets were pre-cleaned with 100% ethyl alcohol (reagent grade) to remove dirt, grease and other contaminants. The one part formulation of coating resin has been diluted with 100% ethyl alcohol to the desired concentration of 1 wt.%. The cleaned nylon sheet was immersed in the coating resin for a period of 1–2 mins. Then, the sheet was carefully removed from the coating resin bath and the excess adhering resin was allowed to drain off. The coating on the nylon sheets was dried by placing them in an oven at 70° C. for 3–4 mins. Then, dried resin coating was then crosslinked by thermal curing at 120° C. for a period of 2 hours. The cured samples were removed from the oven and allowed to cool to room temperature. This procedure was used to coat nylon toothbrush bristles, non-woven nylon and cellulose fibers.

Example 3

Membrane Coating Procedure

Polyethersulfone and nylon membranes were cleaned as described in Example 2 above. The membranes were coated with the antimicrobial resin solution described in Example 1 (1a or 1b) and dried. The coatings then were crosslinked by heating at 120° C. The resulting crosslinked coatings were rinsed with water to remove any unbound polymer, were rinsed with acidified water or buffer [pH2–2.5], followed by another water rinse, then dried. Silver was deposited into the crosslinked polymer matrix by immersing the coated membrane in a 0.05% solution of a silver iodide/potassium iodide complex in aqueous alcohol.

Unbound silver iodide was removed by an ethanol wash. The membrane was rinsed with water, then dried at 70° C. for 30 minutes.

Example 4

Contact Killing Ability

The coated articles described in Example 2 and the membranes described in Example 3 were exposed to a variety of bacteria from the following genera: Pseudomonas, Staphylococcus, Serratia, Klebsiella, Bacillus, Enterococcus and Aspergillus, and a fungus from the genus Candida. The species of microorganisms used are listed in Tables 1 and 2.

The articles and membranes were incubated with the microorganisms at 35°–30° C. for at least 20 hours, and for as long as 504 hours (21 days). The results are shown in Tables 1 and 2:

TABLE 1

Biocidal activity of treated surface

| Organism | Challenge | Time to Kill Complete kill at 30° C. |
|---|---|---|
| Pseudomonas dimunata | $10^6$ CFU/mL | 20 hours |
| Pseudomonas cepacia | $10^6$ CFU/mL | 20 hours |
| Staphylococcus aureus | $10^6$ CFU/mL | 20 hours |
| Serratia marcescens | $10^6$ CFU/mL | 20 hours |
| Escherichia coli | $10^6$ CFU/mL | 20 hours |
| Klebsiella pneumoniae | $10^6$ CFU/mL | 20 hours |
| Bacillus subtilis | $10^6$ CFU/mL | 20 hours |
| Bacillus cerius | $10^6$ CFU/mL | 20 hours |
| Staphylococcus epidermidis | $10^6$ CFU/mL | 72 hours |
| Enterococcus faecalis | $10^6$ CFU/mL | 20 hours |
| Candida albicans | $10^6$ CFU/mL | 168 hours |
| Aspergillus niger | $10^6$ CFU/mL | no growth* |

*21 days at 25° C.

TABLE 2

Bacterial Grow through challenge of treated membranes with $10^6$ CFU/mL Pseudomonas aeruginosa In PBS at 30° C.

| Membrane Type | Days in Test | Days to Failure |
|---|---|---|
| Nylon Membrane, 0.2 μm, untreated control | 32 | 30 |
| Nylon Membrane, 0.2 μm, AMS coated | 54 | None |
| Polyether sulfone 0.2 μm, untreated control | 5 | 3 |
| Polyether sulfone 0.2 μm, AMS coated | 70 | None |

AMS = antimicrobial surface

Example 5

Kinetics of Antimicrobial Action

Figure 3:
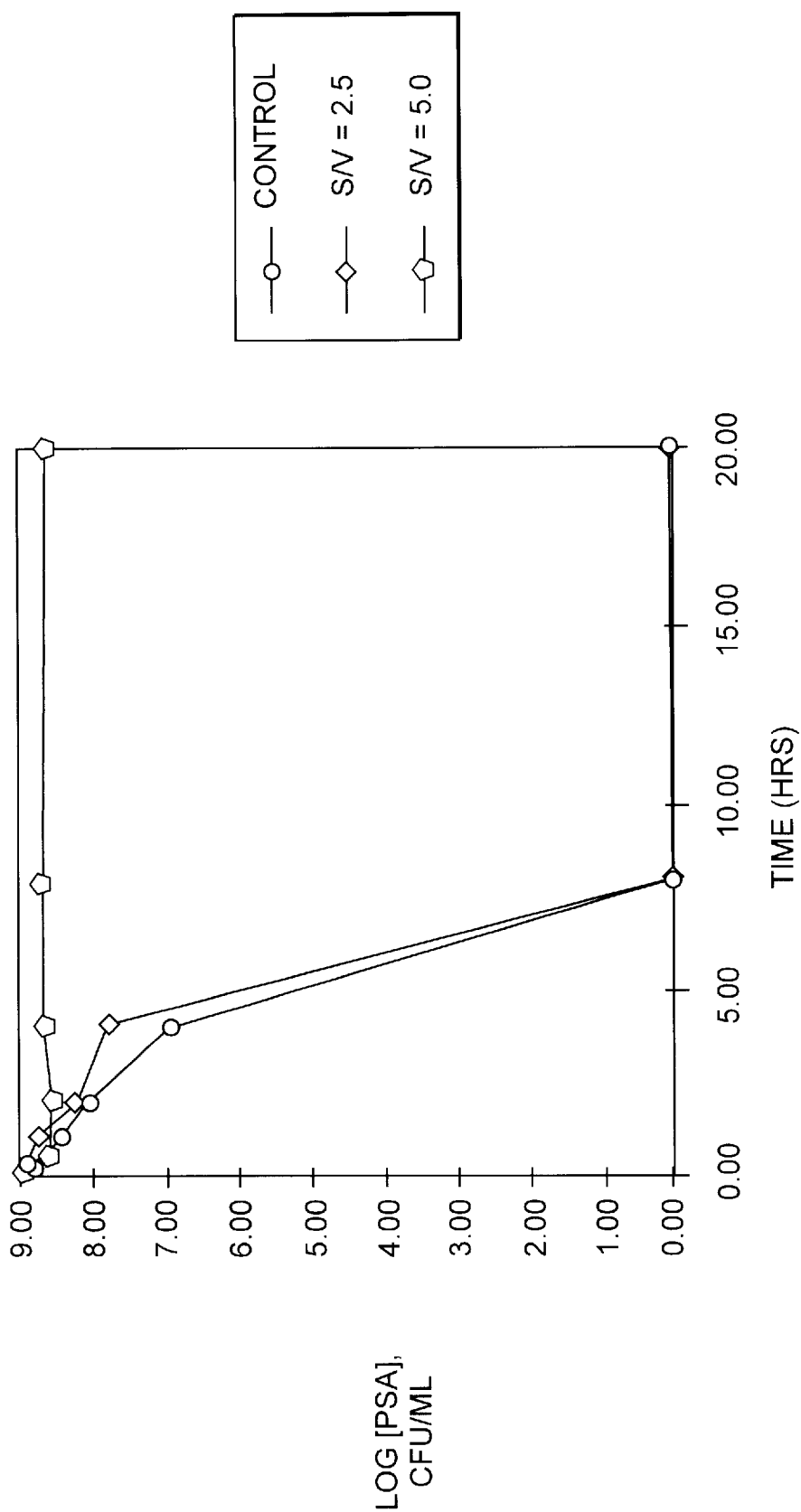
FIG. 3 is a graph illustrating the bioactivity of a preferred coating of the present invention, a matrix formed from crosslinked PHMB complexed with silver salts, treated as a function of surface area to volume against *Pseudonionas aeruginosa* microorganisms in phosphate buffered saline at 30° C.

The coating acts upon contact with the micro-organism, first intercalating into the cell membrane and second transferring the bio-toxic agent directly to the contacting organism. The following time to kill experiment was performed on polyethylene tubes with various diameters coated with the PHMB-BMDGA-silver coating described in Example 1. Coatings were applied as described in Example 2 for the contact lens cases. The tubes were inoculated with predetermined volumes of initial concentrations of up to $10^9$ cfu/mL of Pseudomonas aeruginosa (ATCC#9027) in PBS and incubated at 30° C. for 20 hours. At various time points tubes were sampled and the micro-organism was plated and counted. The treated tubes demonstrated significant antibacterial activity even when volume to surface ratios (S/V) exceeded 4:1. The results are shown in FIG. 3.

Additional evidence for the contact killing mechanism was provided by the following experiment. Polypropylene tubes were coated as described in Example 2 for contact lens cases. The coated tubes and untreated controls were challenged with $10^6$ cfu/ml of *Pseudomonas aeruginosa* in PBS at 30° C. for 20 hours. An organism count by standard plating techniques showed no viable organisms, i.e., a complete elimination (6 log decrease) compared to the untreated tubes.

The solution containing the dead bacteria from the coated tubes was digested in 0.1M nitric acid and analyzed for the presence of silver. Silver concentration was found to be about 600 ppb. A coated tube containing blank PBS (no bacteria) incubated for the same time showed no detectable silver in the solution (less than 10 ppb).

Example 6
Non-leachability of the Coatings

To simulate an aging of approximately 1 year at ambient temperature, membranes with very large surface area were coated as described in Example 3. The coated membranes were immersed in water, isotonic saline and phosphate buffered saline solutions at 70° C. for 5 days. The test solutions were analyzed for elutables by spectroscopic methods with sensitivities less than 10 parts per billion (ppb) of active ingredients, i.e., PHMB, BMDGA, silver and iodide. The following levels were found:

Silver: less than 10 ppb (below detection limit)
PHMB: less than 100 ppb (below detection limit)
BMGDA: less than 300 ppb (below quantitation limit)
Iodide: less than 50 ppb (below quantitation limit)

These analytical results were further confirmed by testing the contact solutions to demonstrate that they show no antimicrobial activity by challenging them with silver sensitive *Escherichia coli (ATCC #8739)* at a concentration of $10^6$ cfu/mL. No decrease in numbers of the microorganism was detected after 20 hours.

Example 7
Toxicity

For assessing mammalian cell toxicity, polypropylene tubes coated as described in Example 2 for contact lens cases, were aged in phosphate buffered saline at 50° C. for 48 hours. Test solutions were evaluated for toxicity with mouse fibroblast cells and showed no toxicity to the cells.

Example 8
Mechanical Strength

Treated surfaces coated as described in Example 2 were subjected to Sutherland rub test with 4PSI for 50 strokes and remained viable while the rubbing surface did not show antimicrobial activity.

Example 9
Inertness

The coating remains fully inert and bio-active after exposure to a variety of physical and chemical stresses:

Low temperature (−15° C.), 24 hours
Ethanol and boiling water, 1 hour
Prolonged exposure to acidic and basic solutions of varying pH (4–10), 12 hours
High ionic strength solution (2% sodium chloride), 24 hours
Autoclaving (121° C. for 15 minutes)
Long term exposure to urine (35° C. for 7 days)
Challenged with 0.7% human serum albumin in phosphate buffered saline in accelerated aging tests (noted a small increase in non-bioavailable silver elutables due to protein complexation) at 80° C. for 72 hours
Exposure to blood products
Worn by human volunteers for a 3 day period. No skin reaction was noted Example 10
Surface Bio-Activity The coating kills micro-organisms on contact—but is non-toxic to mammalian cells. In laboratory testing, treated surfaces (polypropylene, polyethylene, nylon and polyethersulfone) effectively eliminated all human pathogens tested—including bacteria, yeast and fungi.

*Bacillus cereus* (ATCC#11778)-$10^6$ cfu/mL in 20 hours

*Escherichia coli* (ATCC#8739)-$10^6$ cfu/mL in 20 hours

*Pseudomonas aeruginosa* (ATCC#9027)-$10^6$ cfu/mL in 20 hours

*Pseudomonas cepacia* (ATCC#25416)-$10^5$ cfu/mL in 20 hours

*Pseudomonas diminuta* (ATCC#19146)-$10^6$ cfu/mL in 20 hours

*Klebsiella pneumoniae* (ATCC#13883)-$10^6$ cfu/mL in 20 hours

*Staphylococus aureus* (ATCC#6538)-$10^6$ cfu/mL in 20 hours

*Serratia marcescens* (ATCC#8100)-$10^6$ cfu/mL in 20 hours

*Enterococcus faecalis* (ATCC#19433)-$10^6$ cfu/mL in 20 hours

*Staphylococus epidermidis* (ATCC#12228)-$10^5$ cfu/mL in 72 hours

*Candida albicans* (ATCC#10231)-$10^5$ cfu/mL in 168 hours

Surfaces coated as described in Example 2 were challenged with these microorganisms in the initial concentrations indicated. The microorganisms were suspended in phosphate buffered saline and were allowed to remain in contact with the treated surfaces for extended periods at 30° C. The solutions were then analyzed using standard plating methods. While organism growth was documented on untreated surfaces, the microorganisms were completely eliminated on the Surfacine treated samples in the specified time period. These results were confirmed in thousands of tests conducted over three years.

In addition, the treated surfaces were tested against *Aspergillus niger*. No fungal growth was detected over the 28 day test period.

Example 11
Prevention of bio-film formation

To determine efficacy against bio-film formation, polyurethane tubes coated as described in Example 2 and untreated tubes were challenged with a mixture of the following micro-organisms, incubated in a 1% synthetic growth medium at room temperature.: *Pseudomonas diminuta* (ATCC#19146), *Pseudomonas aeruginosa* (ATCC#9027), *Klebsiella pneumoniae* (ATCC#13883), *Bacillus cereus* (ATCC#11778), *Escherichia Coli* (ATCC#8739), *Staphylococcus aureus* (ATCC#6538). Within 24 hours, the micro-organisms in untreated tubes had grown from an initial concentration of $10^4$ cfu/mL to an average of $3 \times 10^5$ cfu/mL. The treated tubes had no viable micro-organisms.

The tubes were then washed and refilled with water. Eight days later, the untreated tubes still yielded $10^5$ cfu/mL (resulting from the bio-film established during the first day of incubation) while the treated tubes yielded no micro-organisms.

Example 12
Antibiotic Resistant Bacteria

Untreated and treated (as described in Example 2) surfaces were challenged with $10^6$ cfu/mL of methicillin and neomycin resistant strain of *Staphylococcus aureus* (ATCC#33592). The micro-organism was suspended in phosphate buffered saline and were allowed to remain in contact with the surfaces. Within 20 hours, treated surfaces had no viable organisms, whereas the number of viable organisms on untreated surfaces remained unchanged.

Equivalents

Those skilled in the art will be able to ascertain, using no more than routine experimentation, many equivalents of the specific embodiments of the invention described herein. These and all other equivalents are intended to be encompassed by the following claims.

What is claimed is:

1. An article of manufacture having disposed on a surface thereof a contact-killing, non-leaching antimicrobial coating which kills microorganisms upon contact, said coating comprising an organic polycationic polymer matrix immobilized on the surface having bound or complexed thereto a surface-accessible antimicrobial metallic material such that the antimicrobial material does not release biocidal amounts of elutables into the surrounding environment;

wherein said organic matrix comprises a biguanide polymer.

2. The article of claim 1 wherein the antimicrobial metallic material is selected from the group consisting of a metal, a metal salt, a metal complex, a metal alloy, and mixtures thereof.

3. The article of claim 2 wherein said metal, metal salt, metal complex, or metal alloy is respectively silver, a silver salt, a silver complex or a silver alloy.

4. The article of claim 2 wherein the metallic material is silver iodide.

5. The article of claim 1 wherein the biguanide polymer is polyhexamethylene biguanide or a polymer containing a biguanide moiety.

6. The article of claim 1 wherein the coating further comprises a crosslinking moiety, and wherein said organic matrix is crosslinked.

7. The article of claim 8 wherein said crosslinking moiety is an organic compound containing functional groups selected from the group consisting of isocyanates, carboxylic acids, acid chlorides, acid anhydrides, succimidyl ethers aldehydes, ketones, alkyl methanesulfonates, alkyl trifluoromethanesulfonates, alkyl para-toluenemethanesulfonates, alkyl halides and epoxides.

8. The article of claim 7 wherein said crosslinking moiety is N,N-bismethylene diglycidylaniline.

9. The article of claim 1 wherein the metallic material is transferred to or taken up by the microorganism when the microorganism contacts the surface.

* * * * *

UNITED STATES PATENT AND TRADEMARK OFFICE
CERTIFICATE OF CORRECTION

PATENT NO. : 5,817,325
DATED : October 6, 1998
INVENTOR(S) : Sawan et al.

It is certified that error appears in the above-identified patent and that said Letters Patent is hereby corrected as shown below:

On the cover sheet, in the text following "[73] Assignees:", delete "Tyngaboro, Mass." and replace with - - Tyngsboro, Mass - -.

On the cover sheet, in the text following "[67] References Cited", under FOREIGN PATENT DOCUMENTS", delete "8176517" and replace with - -8176527 - -.

Signed and Sealed this

Sixteenth Day of March, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO.   : 5,817,325
DATED        : October 6, 1998
INVENTOR(S)  : Sawan et al.

It is certified that error appears in the above-identified patent and that said Letters Patent is hereby corrected as shown below:

At column 1, line 14, above "FIELD OF THE INVENTION", insert:

-- STATEMENT OF GOVERNMENT RIGHTS

This invention was made with government support under Grant No. EY10787, awarded by the Department of Health and Human Services (National Institutes of Health - National Eye Institute). The government has certain rights in the invention. --

Signed and Sealed this

Fourth Day of January, 2000

Attest:

*Attesting Officer*

*Acting Commissioner of Patents and Trademarks*